US007621266B2

(12) United States Patent
Kladders et al.

(10) Patent No.: US 7,621,266 B2
(45) Date of Patent: *Nov. 24, 2009

(54) NOZZLE-SYSTEM FOR A DISPENSER FOR FLUIDS CONSISTING OF A NOZZLE AND A NOZZLE-HOLDER AND/OR SCREW CAP

(75) Inventors: Heinrich Kladders, Muelheim (DE); Herbert Wachtel, Bingen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 466 days.

This patent is subject to a terminal disclaimer.

(21) Appl. No.: 10/757,017

(22) Filed: Jan. 14, 2004

(65) Prior Publication Data
US 2004/0164186 A1  Aug. 26, 2004

Related U.S. Application Data

(60) Provisional application No. 60/440,222, filed on Jan. 15, 2003.

(30) Foreign Application Priority Data
Jan. 14, 2003  (DE) ................................ 103 00 983

(51) Int. Cl.
*A61M 11/00* (2006.01)
(52) U.S. Cl. ............................ 128/200.14; 128/204.25; 128/204.26; 128/200.23; 128/203.12; 128/203.15; 239/118; 239/599; 239/600
(58) Field of Classification Search ............ 128/200.14, 128/204.25, 204.26, 200.23, 203.12, 203.15; 239/600, 599, 118
See application file for complete search history.

(56) References Cited

U.S. PATENT DOCUMENTS

| RE30,486 | E |   | 1/1981  | Beck |
|----------|---|---|---------|------|
| 5,472,143 | A | * | 12/1995 | Bartels et al. ................ 239/462 |
| 5,645,050 | A | * | 7/1997  | Zierenberg et al. ...... 128/203.15 |
| 5,685,485 | A | * | 11/1997 | Mock et al. ............... 239/102.2 |
| 6,497,373 | B2 | * | 12/2002 | Jaeger et al. ................. 239/333 |
| 6,583,627 | B2 | * | 6/2003 | Henning et al. ............. 324/464 |
| 6,764,720 | B2 | * | 7/2004  | Pui et al. ..................... 427/479 |
| 2002/0084290 | A1 |   | 7/2002 | Materna |
| 2005/0077392 | A1 | * | 4/2005 | Geser et al. ................. 239/398 |

FOREIGN PATENT DOCUMENTS

| EP | 0 772 514 B1 | 12/1998 |
| WO | WO 91/14468 | 10/1991 |

(Continued)

OTHER PUBLICATIONS

Abstract for EP 0 772 514: CA 124:346136.

*Primary Examiner*—Patricia Bianco
*Assistant Examiner*—Nihir Patel
(74) *Attorney, Agent, or Firm*—Michael P. Morris; Mary-Ellen M. Devlin; Wendy A. Petka

(57) ABSTRACT

The invention relates to a nozzle system for a delivery device for liquids, which comprises a nozzle and a device which fixes the nozzle in the delivery device. The device has a liquid reservoir from which a liquid is forced through a nozzle under pressure to deliver the liquid. The nozzle is secured by a holder on the delivery device. This holder may itself be secured by a second holder, e.g. in the form of a check nut, or the check nut itself may be the holder. According to the invention at least part of the outer surface of the holding device is micro- or nanostructured.

17 Claims, 8 Drawing Sheets

FOREIGN PATENT DOCUMENTS

| | | |
|---|---|---|
| WO | WO 94/07607 | 4/1994 |
| WO | WO 97/12683 | 4/1997 |
| WO | WO 97/12687 | 4/1997 |
| WO | WO 9712684 A1 * | 4/1997 |
| WO | WO 9712687 A1 * | 4/1997 |
| WO | WO 97/20590 | 6/1997 |
| WO | WO 99/16530 | 4/1999 |
| WO | WO 03/097139 A1 | 12/2003 |

* cited by examiner

NOZZLE-SYSTEM FOR A DISPENSER FOR FLUIDS CONSISTING OF A NOZZLE AND A NOZZLE-HOLDER AND/OR SCREW CAP

CROSS-REFERENCE TO RELATED APPLICATIONS

Benefit of U.S. Provisional Application Ser. No. 60/440,222, filed on Jan. 15, 2003 is hereby claimed, and which application is incorporated herein in its entirety.

BACKGROUND

1. Field of Invention

The invention relates to a nozzle system for a delivery device for liquids which comprises a nozzle and a device which fixes the nozzle in the delivery device. The device has a liquid reservoir from which a liquid is forced through a nozzle under pressure to deliver the liquid. The nozzle is secured by a holder on the delivery device. This holder may itself be secured by a second holder, e.g. in the form of a check nut, or the check nut itself may be the holder. According to the invention at least part of the outer surface of the holding device is micro- or nanostructured.

Preferably, the present invention is part of a propellant-free device for nebulising pharmaceutical fluids. A nebuliser according to the invention is used, for example, to produce an aerosol of droplets for inhalation through the mouth and pharyngeal cavity into the lungs of a patient, for nasal administration or for spraying the surface of the eye.

2. Related Prior Art

WO 91/14468 discloses an apparatus for propellant-free administration of a metered quantity of a liquid pharmaceutical for application by inhalation. A further development of the device is described in detail in WO 97/12687. Reference is specifically made to these publications and the technology described therein is referred to within the scope of the present invention as RESPIMAT® technology. This term refers in particular to the technology which forms the basis for a device according to FIGS. 6a and 6b of WO 97/12687 and the associated description.

In an inhaler of this kind liquid pharmaceutical formulations are stored in a reservoir. From there, they are conveyed through a riser tube into a pressure chamber from where they are forced through a nozzle. The nozzle has a liquid inlet side and a liquid outlet side. On the liquid inlet side is an opening through which a liquid from the pressure chamber can enter the nozzle. On the opposite side, the end face of the nozzle, the liquid then passes through two nozzle apertures which are aligned so that the jets of liquid leaving the apertures strike one another and are thereby atomised. The nozzle apertures are arranged in the inhaler in such a way that they are in direct contact with the outer environment. These inhalers normally deliver formulations based on water or mixtures of water and ethanol. They are able to nebulise a small amount of a liquid formulation in the therapeutically required dosage within a few seconds to produce an aerosol suitable for therapeutic inhalation. With the device, quantities of less than 100 microlitres can be nebulised, e.g. with one spray actuation, to produce an aerosol with an average particle size of less than 20 microns so that the inhalable part of the aerosol corresponds to the therapeutically effective amount. In these nebulisers with RESPIMAT® technology a pharmaceutical solution is converted by high pressure up to 500 bar into a low-speed aerosol mist destined for the lungs, which the patient can then breathe in.

A small amount of the liquid may be deposited from the outside as a film or as an accumulation of small droplets on the end face of the nozzle or on the end face of the fixing means for the nozzle or on the inside of the mouthpiece. This fraction of the liquid is also referred to as the mouthpiece fraction within the scope of this specification.

The amount of liquid deposited need not be constant in every spray actuation but may depend on numerous factors such as the spatial orientation of the device during the aerosol production or the ambient temperature, relative humidity, etc. This leads on the one hand to a certain variability, however minor, in the amount dispensed which is then available for the patient to take in. The liquid deposited may also cause contamination of the outer surface of the nozzle system or of the mouthpiece, which may in turn affect the pharmaceutical quality of the next aerosol mist.

Although these two effects are only slight in devices using RESPIMAT® technology it is important for reasons of quality control to minimise such effects.

It has now surprisingly been found that in devices for dispensing liquids the proportion of liquid deposited on the outside of the nozzle system can be reduced if the corresponding surfaces are at least partially micro- or nanostructured. Devices based on the RESPIMAT® technology are preferred.

SUMMARY OF THE INVENTION

It is an objective of the invention to reduce the variability of the proportion of the liquid delivered by means of a device for delivering pharmaceutical liquids, such as atomisers, inhalers, etc.

A further aim of the invention is to reduce the proportion of liquid which is deposited, from an aerosol mist, on the device for delivering the pharmaceutical liquid.

A further aim is to optimise the quality of delivery of a liquid using atomisers having the RESPIMAT® technology.

In accordance with one or more embodiments of the present invention, a nozzle for a delivery device for fluids includes an inlet side and an outlet side wherein an outer surface of the outlet side includes at least one of microstructures and nanostructures.

By way of example, a nozzle system for a device for delivering fluids may include: a nozzle having one or more nozzle openings and an outer surface at a fluid outlet side of the nozzle; a nozzle holder which comprises a through-bore having a sidewall initiating at a position in communication with the one or more nozzle openings of the fluid outlet side of the nozzle, and terminating at an end face of the nozzle holder, wherein at least one of the following surfaces include at least one of microstructures and nanostructures: the outer surface of the fluid outlet side of the nozzle, an outer surface of the end face of the nozzle holder, or the side wall of the through-bore of the nozzle holder.

Preferably, the through-bore of the nozzle holder widens out continuously from the one or more nozzle openings to the end face thereof.

The nozzle system may further include a check nut engaging the nozzle holder and having an end face and a bore including a side wall thereof, which communicates with the through-bore of the nozzle holder and widens out continuously therefrom, wherein at least one of an outer surface of the end face of the check nut and the side wall of the bore of the check nut include at least one of microstructures and nanostructures.

Further, a side of the through-bore that is remote from the one or more nozzle openings may include at least one of microstructures and nanostructures.

The microstructures or nanostructures may include surface structure elevations and/or depressions with a height/depth of 0.1 to 100 microns. The spacing between the elevations and depressions may be in the range from 0.1 to 200 microns. At least 20% of the corresponding surface may include the microstructures or nanostructures.

DETAILED DESCRIPTION OF THE INVENTION

Figure 1A:
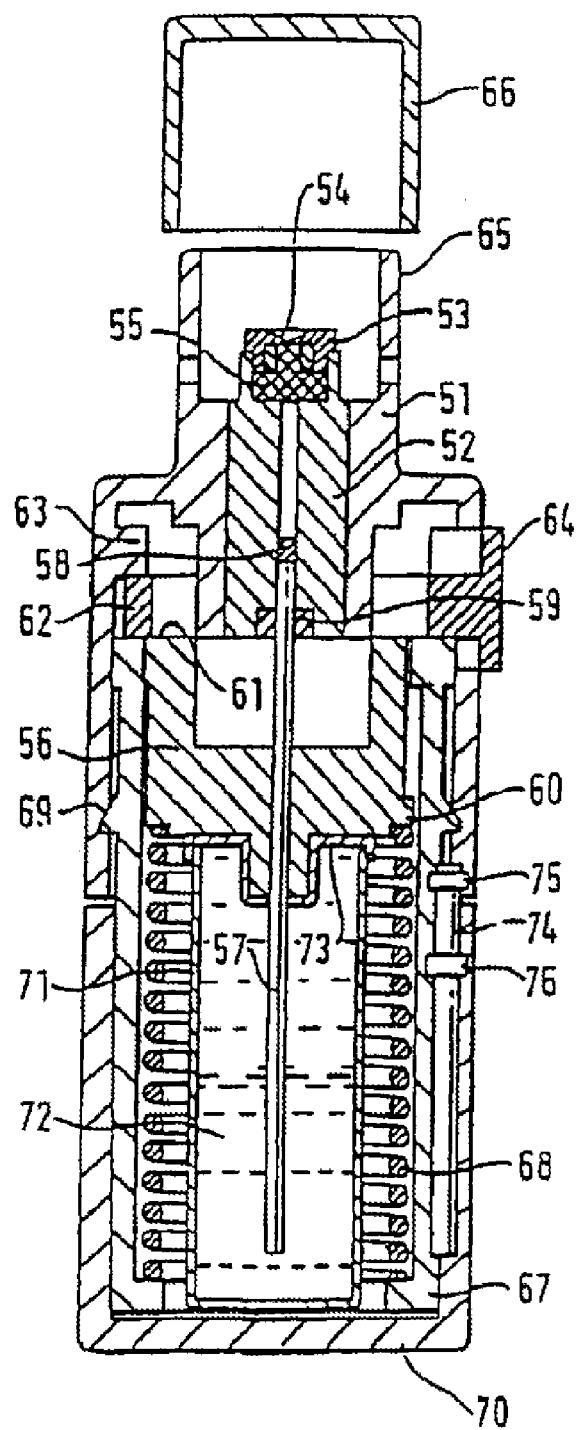
FIGS. 1a/b, show the RESPIMAT® nebuliser with which the aqueous aerosol preparations according to the invention may advantageously be inhaled.

The present invention relates to a nozzle system for liquid nebulisers wherein at least part of the outer surface of the nozzle system or other components of the nebuliser which may come into contact with the aerosol delivered have a micro- or nanostructured surface. Preferably at least the end face of the nozzle facing outwards (i.e. the side of the nozzle from which the aerosol mist emerges) and/or the similarly oriented side of the device for holding the nozzle is provided with a surface structure of this kind.

In the simplest case the nozzle is a perforated plate with at least one opening.

Other embodiments with a more complicated constructions relate to nozzles consisting of at least two superimposed plates, at least one of the plates having a second microstructure so that the superimposed plates define on one side a liquid inlet adjoining a channel system and/or a filter system which then opens into one, two or more liquid outlets.

In embodiments of the nozzle having a plurality of nozzle apertures, preferably all of them are formed on a common side. In such cases the nozzle apertures may be oriented so that the jets of liquid emerging from them meet in front of the nozzle aperture. Systems of this kind require nozzles with at least two apertures. Nozzles of this kind are described in more detail in the description of RESPIMAT® technology.

These or other nozzles may be part of a nozzle system by means of which the nozzles are held at a defined place in the delivery device. A nozzle system of this kind consists of a nozzle and a nozzle holder and/or a check nut, each having an end face. This is the side which is oriented away from the side of the nozzle having the nozzle aperture, i.e. it faces outwards. The inside of the end face of the nozzle holder or the check nut comes into contact with the liquid outlet side of the nozzle and thereby exerts the force needed to secure the nozzle in the direction of the liquid inlet side of the nozzle. The end face of the nozzle holder and/or of the check nut has or have a through-bore or hole through which the aerosol can escape from the nozzle. Therefore, the nozzle apertures are in, or in a direct line below, the bore.

The bore or the hole may be constructed as an inner recess which widens continuously from the nozzle apertures. Embodiments of the nozzle system wherein the recess is funnel-shaped, preferably conical, are advantageous.

In nozzles having at least two nozzle apertures orientated so that the two jets of liquid leaving the nozzle body meet, the point of impact, the point where the jets of liquid meet and are atomised to form an aerosol, is preferably located close to the base of the recess, i.e. in the region of the nozzle aperture. It is obvious that in such a case the recess is one of the areas particularly at risk of liquid being deposited thereon.

According to the invention, at least part of the following surfaces is micro- or nanostructured:
the outer surface of the liquid outlet side of the nozzle and/or
the outer surface of the end face of the nozzle holder and/or
the side wall of the bore or hole of the nozzle holder and/or
the outer surface of the end face of the check nut and/or
the side wall of the bore or hole of the check nut.

Preferably, the widening recess of the nozzle holder and/or of the check nut or a combination of the two parts has the micro- or nanostructured surface, in particular.

These areas and/or the outer surface of the nozzle outlet side and optionally other surfaces close to the nozzle opening on which the liquid from the aerosol mist is most likely to be deposited are also referred to as critical surfaces within the scope of the present invention.

In the case of inhalers, the critical surfaces also include the mouthpiece, into which a nozzle usually sprays the pharmaceutical aerosol so that it can then be inhaled. A mouthpiece of this kind may be constructed as a tubular projection on the base of which is located the nozzle.

EP 772514 describes how the micro- or nanostructures used according to the invention might look and therefore reference is hereby made to the contents of this publication.

If the critical surfaces are those of the nozzle holder or check nut, at least 20% of its surface, more preferably at least 50% and most preferably at least 75% is micro- or nanostructured.

Alternatively and/or in addition, 20% of the outer surface of the nozzle outlet side, more preferably 50% and most preferably at least 75% is micro- or nano-structured.

If the critical surface is the inner surface of a mouthpiece, this surface may also be at least 20% micro- or nano-structured, more preferably at least 50% and most preferably at least 75%.

Which surfaces are to be regarded as critical in any individual case depends on the particular device and can be discovered by simple tests.

Preferably, the critical surfaces of the nozzle holder and/or check nut are micro- or nano-structured.

The structuring of the critical surface according to the invention is achieved by providing elevations and depressions on a micro or nano scale at least on areas of the critical inner surface.

The elevations and depressions may be in the form of peaks, spheres, flat surfaces, wedge shapes, hemispherical shapes, etc.

They may be randomly arranged or ordered, e.g. in circles, rows, in a zigzag, meandering, etc.

The spacing between the raised portions on the surface structure is in the range from 0.1 to 200 microns, preferably 0.1 to 100 microns. Distances of 0.1 to 10 microns are preferred, while distances of 0.1 to 1 micron are even more preferred.

The height of the elevations or the depth of the depressions are in the range from 0.1 to 100 microns, preferably 0.1 to 50 microns. Spacings of 0.1 to 10 microns are most preferred.

Preferably the elevations of the surface structures are close enough together to ensure that hydrophilic drops of liquid, e.g. drops of water, roll off the elevations without actually touching the underlying area. At the same time the elevations of the surface structures should not be too close together or the depressions should not be too flat so as not to form a sealed surface, with respect to the droplet size of the liquid, in which the surface forces between the drops and the surface come into effect fully. It is therefore desirable that the height of the elevations from the base should increase as the distance between the elevations increases. Preferably, the surfaces have elevations measuring 0.1 to 50 microns wherein the spacing between the elevations is 0.1 to 100 microns.

Particularly preferred are structures having two differently graduated surface modulations such as may be obtained by superimposing a submicroscopic roughness with a periodic length of 0.05 to 0.5 microns and a roughness with a periodic length of 0.05 to 10 microns.

Preferably, the critical surfaces consist of hydrophobic materials or materials which have been given a durable hydrophobic finish or they are coated with such materials and the raised portions cannot be detached by water or water-containing detergents. The materials used may be plastics, metals, ceramics, glass, etc.

Preferred materials are glass and/or ceramics and/or metals and/or plastics such as polyethylene, polypropylene, polycarbonate, polyacrylates, polyesters, silanes, etc. Plastics are preferred. If desired, a plastic of this kind may be provided with a coating of another plastic which carries or forms the surface structure, e.g. when dried.

Structured surfaces of this kind may either be produced by forming the surface structures during the manufacture from hydrophobic materials or by subsequently subtracting or adding material to the surfaces. These processes include subsequent stamping, etching, laser ablation, galvanic machining, adhesive bonding of a structured film, adhesive bonding of a powder, spraying with suspensions, depositing sublimates, etc.

Finally, it is possible to create surfaces of this kind on objects by subsequent provision of a durable hydrophobic surface on previously produced surfaces with the desired structures.

One possible way of subsequently making a surface durably hydrophobic is by subsequently silanising surfaces with the desired structures which have been prepared beforehand. Silanising may be carried out on any materials which are naturally hydrophilic but capable of reacting with the reactive groups of the silanes so that finally the surface consists of the hydrophobic groups of the silanes.

In order to produce the desired surface structures during the actual manufacture from hydrophobic polymers the objects may be produced in moulds which contain the negative of the desired surface structure.

It is also possible to apply the hydrophobic polymers in the form of solutions and/or dispersions which produce the desired surface structures when dried and cured.

Such structures are formed for example from self-organising polymers or under conditions as known in principle from the manufacture of matt paint surfaces.

If it is not possible or not desirable to create the desired surface structures from the outset, this may also be done subsequently, e.g. by subsequent stamping or etching. Stamping may be carried out, for example, using heated or heatable stamps. The etching may be carried out using the known means for chemical etching or by physical methods such as ion etching with oxygen or other irradiation which leads to roughening of the surface and a surface structure which can be used according to the invention.

The method by which a surface structure is produced depends on the material used and the desired micro-structure.

This invention is preferably used in a nebuliser using RESPIMAT® technology.

The preferred atomiser essentially comprises a lower and an upper housing mounted to be rotatable relative to one another, the upper part of the housing containing a spring housing with spring which is tensioned by rotating the two housing parts by means of a locking clamping mechanism preferably in the form of a screw thread or gear and is released by pressing a release button on the upper part of the housing. This moves a power take-off flange connected to a hollow piston on the lower end of which a container can be fitted and at the upper end of which are found a valve and a pressure chamber which is connected for fluid transmission to the nozzle or the nozzle system formed in the upwardly open part of the upper housing part. The liquid is sucked in by the hollow piston and pumped to the pressure chamber from where it is expelled through the nozzle in the form of an aerosol.

The hollow piston with valve body corresponds to a device disclosed in WO 97/12687. It projects partially into the cylinder of the pump housing and is disposed to be axially movable in the cylinder. Reference is made particularly to FIGS. 1-4—especially FIG. 3—and the associated parts of the description. At the moment of release of the spring the hollow piston with valve body exerts, at its high pressure end, a pressure of 5 to 60 Mpa (about 50 to 600 bar), preferably 10 to 60 Mpa (about 100 to 600 bar) on the fluid, the measured amount of active substance solution.

The valve body is preferably mounted at the end of the hollow piston which faces the nozzle body. The valve body is connected for fluid transmission with the nozzle.

The nozzle in the nozzle body is preferably microstructured, i.e. produced by microtechnology. The microstructure mentioned in this context is, however, different from the microstructure according to the invention, at least in terms of its function, as will be clear from the context. Microstructured nozzle bodies are described for example in WO 94/07607 or WO 99/16530. Another embodiment is disclosed in WO 03/097139. Reference is hereby made to all the documents. With regard to WO 94/07607 we refer particularly to FIG. 1 and the associated description.

The nozzle body consists, for example, of two sheets of glass and/or silicon firmly attached to one another, at least one of these sheets having one or more microstructured channels which connect the nozzle inlet side to the nozzle outlet side. On the nozzle outlet side there may be at least one round or non-round opening 2 to 10 microns deep and 5 to 15 microns wide, the depth preferably being 4.5 to 6.5 microns and the length preferably being 7 to 9 microns.

In the case of a plurality of nozzle openings, preferably two, the directions of spraying of the nozzles in the nozzle body may run parallel to one another or be inclined relative to one another in the direction of the nozzle opening. In a nozzle body with at least two nozzle openings on the outlet side, the directions of spraying may be inclined at an angle of 20 to 160° to one another, preferably 60 to 150, most preferably 70 to 100°.

The nozzle openings are preferably arranged at a spacing of 10 to 200 microns, more preferably at a spacing of 10 to 100 microns, most preferably 30 to 70 microns. A spacing of 50 microns is most preferred. The directions of spraying consequently meet in the region of the nozzle openings.

For the sake of simplicity an embodiment will now be described wherein only the base part of the nozzle body has relief-like microstructures, but the top part does not. In other embodiments the situation is reversed or both parts may have these microstructures.

On the base part, on the flat surface, there may be a set of channels to create a plurality of filter routes (filter channels) in collaboration with the substantially flat surface of the top part. The base part may have a fill chamber the top of which is again formed by the top part. This fill chamber may be provided before or after the filter channels. It is also possible to have two fill chambers of this kind. Another set of channels on the substantially flat surface of the base part which is provided downstream of the filter channels forms, together with the top part, a set of channels which create a plurality of nozzle outlet routes.

Preferably, the overall cross sectional area of the nozzle outlets is 25 to 500 square micrometres. The total cross sectional area is preferably 30 to 200 square micrometres.

In another embodiment this nozzle construction has only one nozzle aperture.

In other embodiments of this kind the filter channels and/or the fill chamber are omitted.

Preferably, the filter channels are formed by projections arranged in a zigzag shape. Thus, for example, a zigzag configuration of this kind is formed by at least two rows of projections. A number of rows of projections may also be formed, the projections being laterally offset from one another in order to construct additional rows which are skewed relative to these rows, these additional rows forming the zigzag configuration. In embodiments of this kind the inlet and outlet may each have a longitudinal slot for unfiltered or filtered fluid, each of the slots being substantially the same width as the filter and substantially the same height as the projections on the inlet and outlet sides of the filter. The cross section of the throughflow passages formed by the projections may be perpendicular to the direction of flow of the fluid and may decrease from row to row, viewed in the direction of flow. Also, the projections arranged closer to the inlet side of the filter may be larger than the projections arranged closer to the outlet side of the filter. Additionally, the spacing between the base part and top part may taper in the region from the nozzle inlet side to the nozzle outlet side. The zigzag configuration which is formed by the minimum of two rows of projections has an angle of inclination a of preferably 20° to 250°.

Further details of this nozzle construction may be found in WO-94/07607. Reference is hereby made specifically to this publication, particularly FIG. 1 and the associated description.

The nozzle may be embedded in an elastomeric sleeve as described in WO 97/12683. In its simplest form a sleeve of this kind is a ring or member having an opening into which the nozzle can be inserted. This opening surrounds the nozzle block over its entire outer surface, i.e. the surface which is perpendicular to the preferably linear axis formed by the nozzle inlet side and the nozzle outlet side. The sleeve is open at the top and bottom so as not to impede either the supply of liquid to the nozzle inlet side of the nozzle or the delivery of the liquid. This sleeve may in turn be inserted in a second sleeve. The external form of the first sleeve is preferably conical. The opening of the second sleeve is shaped accordingly. The first sleeve may be made of an elastomer.

The nozzle, optionally including the sleeve, is secured by a device for holding it from the outside in the direction of the hollow piston, as described above.

The locking clamping mechanism of the atomiser contains a spring, preferably a cylindrical helical compression spring, as a store for the mechanical energy. The spring acts on the power take-off flange as a spring member the movement of which is determined by the position of a locking member. The travel of the power take-off flange is precisely limited by an upper stop and a lower stop. The spring is preferably tensioned via a stepping-up gear, e.g. a helical sliding gear, by an external torque which is generated when the upper housing part is turned relative to the spring housing in the lower housing part. In this case, the upper housing part and the power take-off flange contain a single- or multi-speed spline gear.

The locking member with the engaging locking surfaces is arranged in an annular configuration around the power take-off flange. It consists for example of a ring of plastics or metal which is inherently radially elastically deformable. The ring is arranged in a plane perpendicular to the axis of the atomiser. After the tensioning of the spring, the locking surfaces of the locking member slide into the path of the power take-off flange and prevent the spring from being released. The locking member is actuated by means of a button. The actuating button is connected or coupled to the locking member. In order to actuate the locking clamping mechanism the actuating button is moved parallel to the annular plane, preferably into the atomiser, and the deformable ring is thereby deformed in the annular plane. Details of the construction of the locking clamping mechanism are described in WO 97/20590.

The lower housing part is pushed axially over the spring housing and covers the bearing, the drive for the spindle and the storage container for the fluid.

When the atomiser is operated, the upper part of the housing is rotated relative to the lower part, the lower part taking the spring housing with it. The spring meanwhile is compressed and biased by means of the helical sliding gear, and the clamping mechanism engages automatically. The angle of rotation is preferably a whole-number fraction of 360 degrees, e.g. 180 degrees. At the same time as the spring is tensioned, the power take-off component in the upper housing part is moved along by a given amount, the hollow piston is pulled back inside the cylinder in the pump housing, as a result of which some of the fluid from the storage container is sucked into the high pressure chamber in front of the nozzle.

If desired, a plurality of replaceable storage containers containing the fluid to be atomised can be inserted in the atomiser one after another and then used. The storage container contains the aqueous aerosol preparation according to the invention.

The atomising process is initiated by gently pressing the actuating button. The clamping mechanism then opens the way for the power take-off component. The biased spring pushes the piston into the cylinder in the pump housing. The fluid emerges from the nozzle of the atomiser in the form of a spray. The liquid pharmaceutical preparation hits the nozzle body at an entry pressure of up to 600 bar, preferably 200 to 300 bar and is atomised through the nozzle openings into an inhalable aerosol. The preferred particle sizes of the aerosol are up to 20 microns, preferably 3 to 10 microns.

Volumes of 10 to 50 microlitres are preferably delivered, volumes of 10 to 20 microlitres are more preferable, whilst a volume of 15 microlitres per spray is particularly preferred.

Further details of construction are disclosed in PCT applications WO 97/12683 and WO 97/20590, to which reference is made hereby.

The components of the atomiser (nebuliser) consist of a material which is suited to its purpose. The housing of the atomiser and—insofar as the operation allows—other parts are also preferably made of plastics, e.g. by injection moulding. For medical uses, physiologically harmless materials are used.

Preferably, a nebuliser according to the invention is cylindrical in shape and has a handy size of less than 9 to 15 cm long and 2 to 4 cm wide, so that it can be carried anywhere by the patient.

As already mentioned, according to the invention, in a device of the RESPIMAT® type, the outer surface of the nozzle outlet side, parts of the nozzle holder and/or the check nut and optionally other surfaces close to the nozzle opening onto which liquid from the aerosol mist delivered is most likely to be deposited, may be provided with the nano- or microstructure. Additionally or alternatively, other surfaces of the RESPIMAT® device may also have the nano- or microstructure according to the invention. These include the inner surface and parts of the outer surface of the hollow piston, the inner surfaces of the components that make up the nozzle, parts of the inner microstructured surface of the nozzle and others.

The present invention may be applied to all kinds of liquid nebulisers in which aqueous systems are nebulised. The invention is not limited either to the technology on which the nebulisation is based nor to the purpose for which nebulisers of this kind are to be used.

Figure 1B:
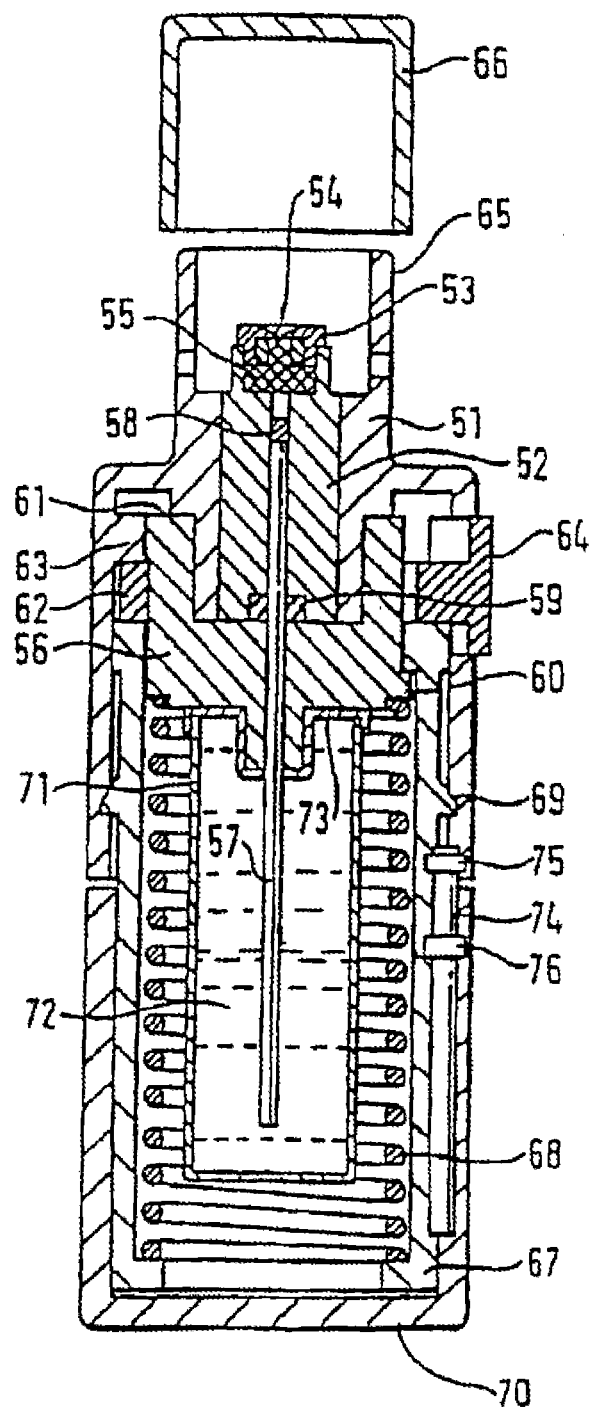

FIG. 1a shows a longitudinal section through the atomiser with the spring tensioned. FIG. 1b shows a longitudinal section through the atomiser with the spring relaxed.

The upper housing part (51) contains the pump housing (52), on the end of which is mounted the holder (53) for the atomiser nozzle. In the holder is the expanding recess (54) and the nozzle body (55). The hollow piston (57) fixed in the power take-off flange (56) of the locking clamping mechanism projects partly into the cylinder of the pump housing. At its end the hollow piston carries the valve body (58). The hollow piston is sealed off by the gasket (59). Inside the upper housing part is the stop (60) on which the power take-off flange rests when the spring is relaxed. Located on the power take-off flange is the stop (61) on which the power take-off flange rests when the spring is under tension. After the tensioning of the spring, the locking member (62) slides between the stop (61) and a support (63) in the upper housing part. The actuating button (64) is connected to the locking member. The upper housing part ends in the mouthpiece (65) and is closed off by the removable protective cap (66).

The spring housing (67) with compression spring (68) is rotatably mounted on the upper housing part by means of the snap-fit lugs (69) and rotary bearings. The lower housing part (70) is pushed over the spring housing. Inside the spring housing is the replaceable storage container (71) for the fluid (72) which is to be atomised. The storage container is closed off by the stopper (73), through which the hollow piston projects into the storage container and dips its end into the fluid (supply of active substance solution).

The spindle (74) for the mechanical counter (optional) is mounted on the outside of the spring housing. The drive pinion (75) is located at the end of the spindle facing the upper housing part. On the spindle is the slider (76).

Figure 2A:
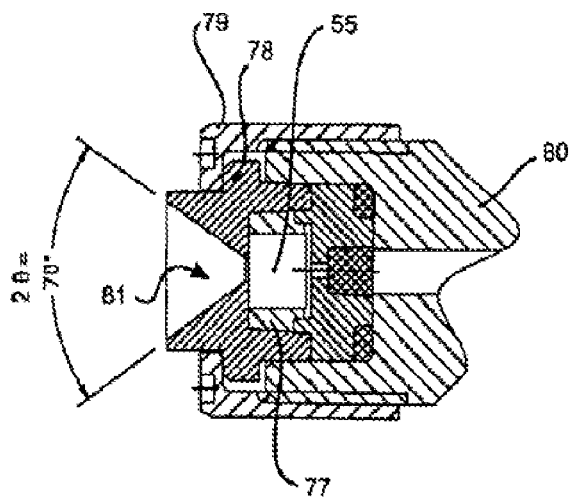
FIG. 2 shows two embodiments of a nozzle system in side elevation, partly in section.

FIG. 2a shows an embodiment of the system comprising the nozzle (55) and nozzle holder in side elevation, partly in section.

The nozzle (55) or nozzle holder as a self-contained component unit—a so-called uniblock—is mounted in a conical sleeve (77) which is itself in turn placed in the nozzle holder (78). The nozzle holder (78) is braced on the housing (80) by means of a check nut (79) and the nozzle (55) is finally fixed thereto.

At the same time the check nut (79) holds the nozzle holder (78) from outside without engaging in the conical recess (81) thereof. The recess (81) is conical in shape, in that it widens out continuously as its distance from the nozzle apertures increases. The recess (81) has a cone angle 2θ.

Because the check nut (79) does not engage in the nozzle holder (78) from outside, the recess (81) is formed exclusively by the nozzle holder (78).

Figure 2B:
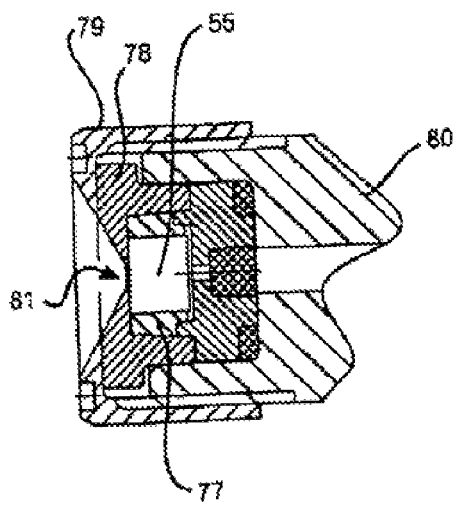

FIG. 2b shows an embodiment of the nozzle system (55) in side view, partly in section, which differs from FIG. 2a in that this time the check nut also forms part of the conical recess (81). There are no steps of any kind in the recess (81) in the region of the transition from the nozzle holder (78) to the check nut (79). The particles of the nebuliser mist which then accumulate in such a step and contribute to the mouthpiece fraction can no longer be picked up by a fresh actuation of the nebuliser.

FIG. 3—Example

A RESPIMAT® device is used, analogously to FIG. 1. This device has been modified so that the critical surface, i.e. the recess (81), of the nozzle system analogously to that of FIG. 2 has been coated with the silicon paint Lotusan® made by Messrs Dyckerhoff.

Then an aqueous placebo solution is sprayed using the device and the quantity of liquid deposited on the critical surface is measured by comparison with an uncoated apparatus.

Figure 3:
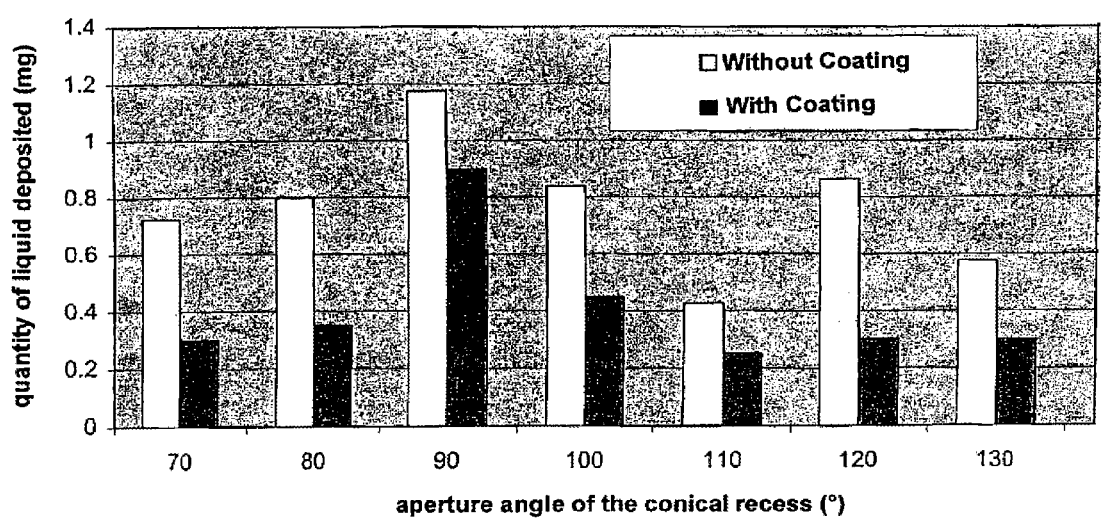
FIG. 3 shows an experimental example of a microstructured nozzle system.

The test is repeated for a number of devices with different angles of opening of the conical recess (FIG. 3).

The tests show that the microstructuring of the critical surface of the nozzle system advantageously reduces the quantity of liquid deposited on the critical surface, compared with a smooth nozzle system.

Figure 4:
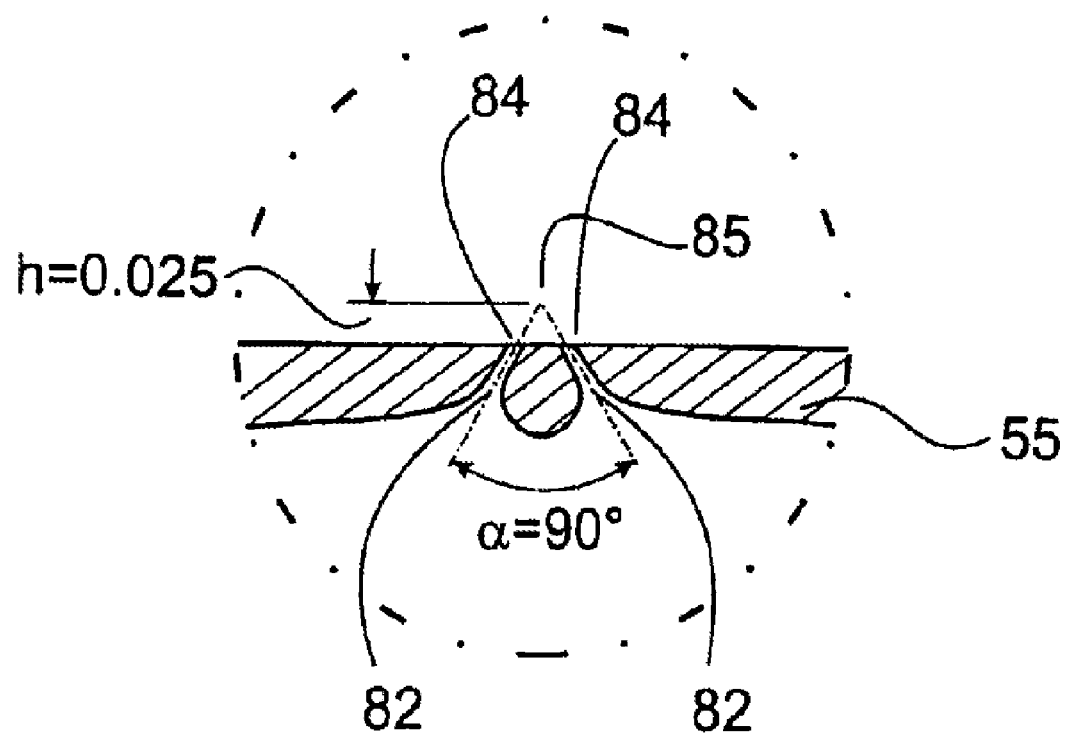
FIG. 4 shows a diagrammatic representation of an embodiment of a nozzle body in side view, in section.
Figure 5:
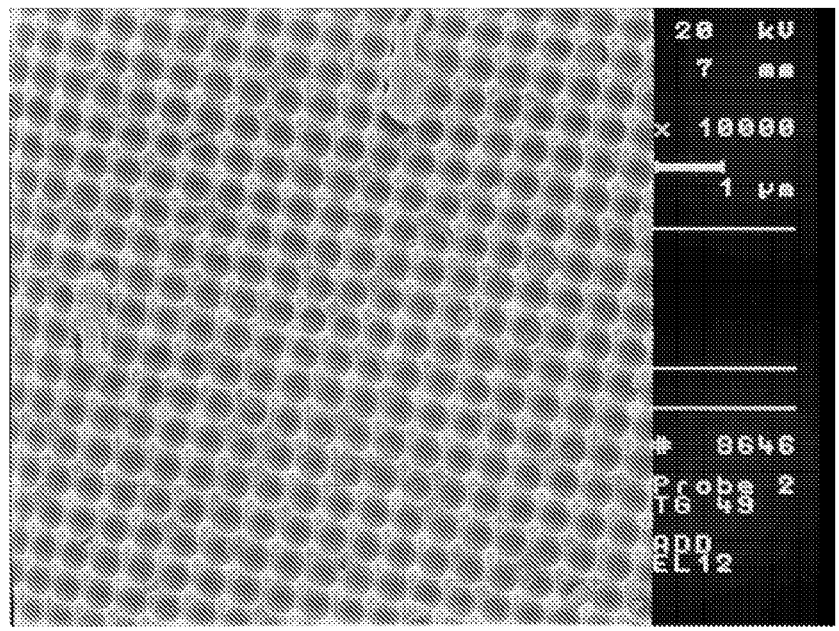
FIGS. 5 to 9 show surface structures of polyester films with a structured acrylic layer.
Figure 6:
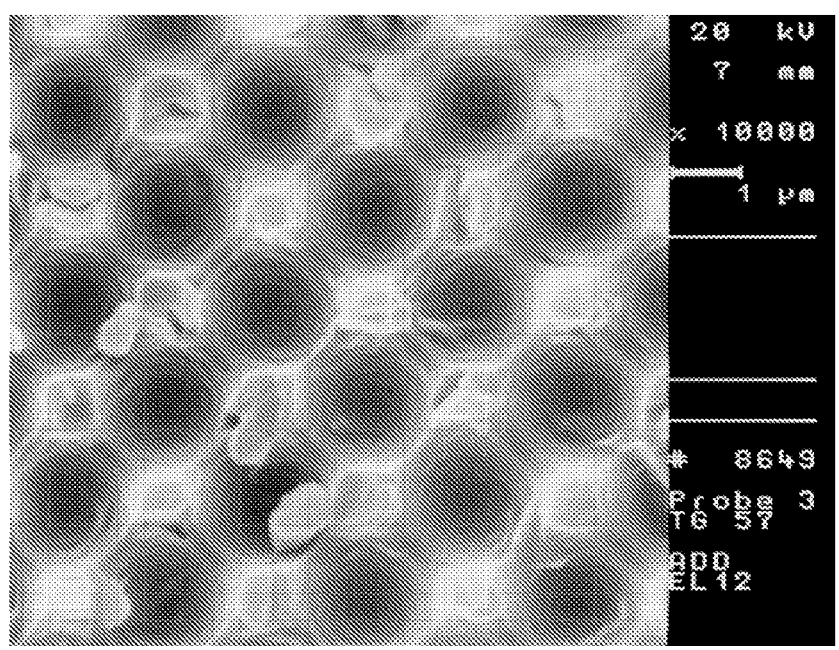
Figure 7:
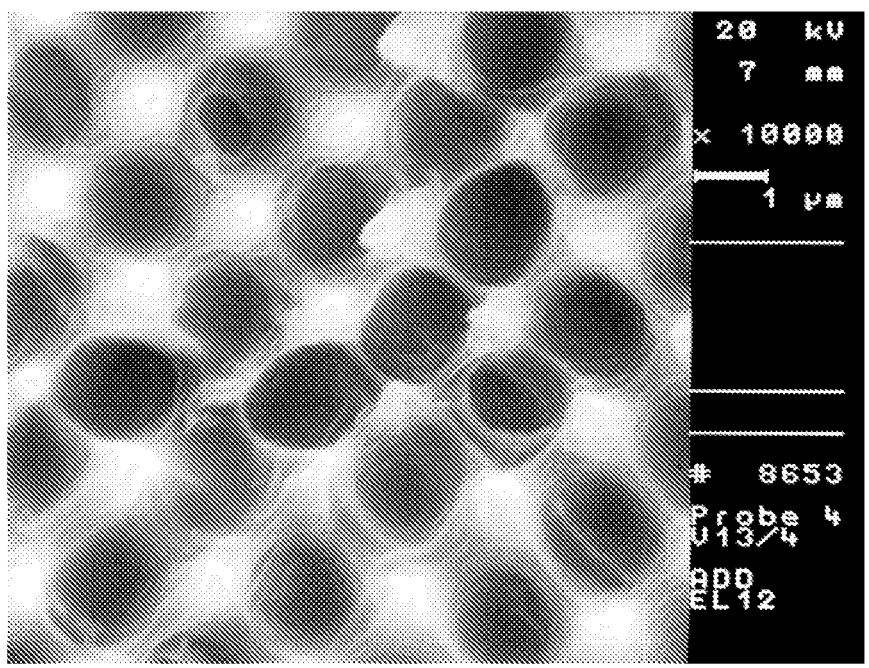
Figure 8:
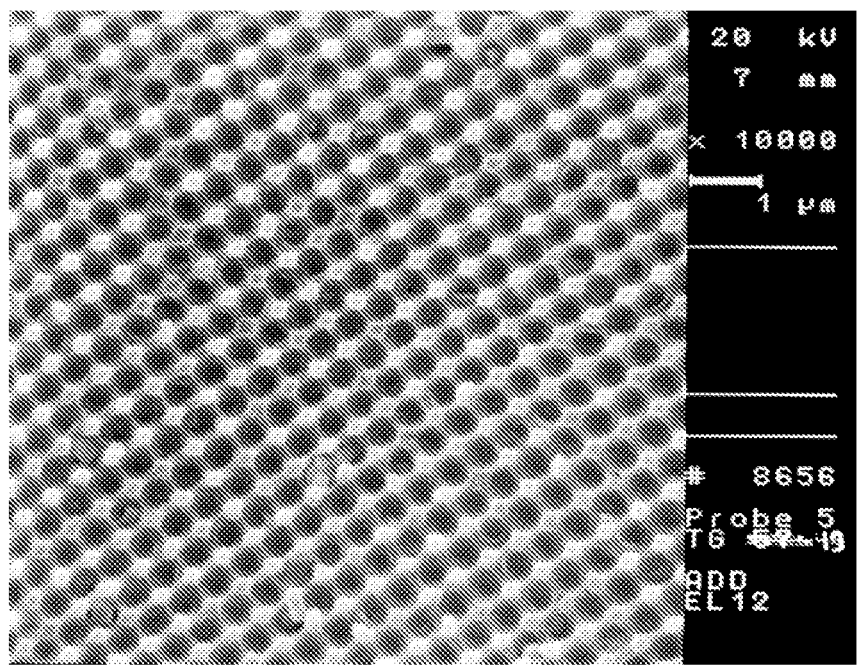
Figure 9:
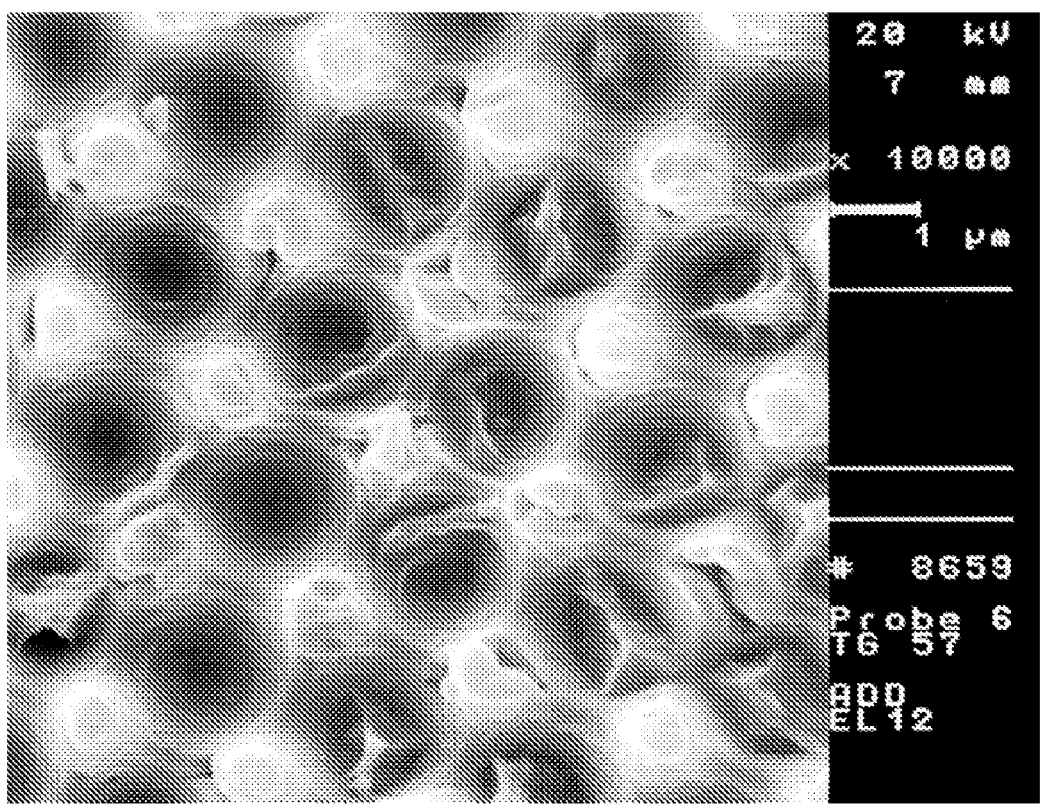

FIG. 4 is a diagrammatic view of a detail of an embodiment of a nozzle member (55) with two nozzle openings shown in sectional side view.

The two nozzle channels (82) are arranged so that the jets leaving the nozzle apertures (84) of the nozzle channels meet at the point of collision (85) at an angle $\alpha=90°$. The point of collision (85) has a height of impact $h=25$ μm above the nozzle apertures.

FIGS. 5 to 9 show examples of surface structures of polyester films with a structured acrylic layer which may be adhered to the critical surface of the nozzle holder and/or the check nut.

Film 1 with structures in the region of 0.5 microns,

Film 2 with structures in the region of 2 microns,

Film 3 with structures in the region of 2 microns and 10 microns of superstructure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A nozzle for a delivery device for fluids comprising:
an inlet side;
an outlet side, including at least one nozzle opening; and
at least two superimposed plates, at least one of the plates produced by microtechnology, so that the plates lying one on top of the other define, on one side, a fluid inlet connected to a channel system and/or a filter system which then opens into one or more fluid outlets,
wherein an outer surface of the outlet side includes at least one of elevation and/or depression microstructures and elevation and/or depression nanostructures, which do not include the at least one nozzle opening.

2. The nozzle according to claim 1 comprising at least two nozzle openings oriented so that the jets of fluid emerging from them intersect.

3. The nozzle according to claim 1 wherein the nozzle has at least two nozzle outlets oriented towards one another.

4. A nozzle system for a device for delivering fluids, comprising:
   a nozzle having one or more nozzle openings and an outer surface at a fluid outlet side of the nozzle;
   at least two superimposed plates at least one of the plates produced by microtechnology, so that the plates lying one on top of the other define, on one side, a fluid inlet connected to a channel system and/or a filter system which then opens into one or more fluid outlets; and
   a nozzle holder which comprises a through-bore having a sidewall initiating at a position in communication with the one or more nozzle openings of the fluid outlet side of the nozzle, and terminating at an end face of the nozzle holder, wherein:
   at least one of the following surfaces include at least one of elevation and/or depression microstructures and elevation and/or depression nanostructures, which do not include the one or more nozzle openings:
      the outer surface of the fluid outlet side of the nozzle,
      an outer surface of the end face of the nozzle holder, or
      the side wall of the through-bore of the nozzle holder.

5. The nozzle system according to claim 4 wherein the through-bore of the nozzle holder widens out continuously from the one or more nozzle openings to the end face thereof.

6. A nozzle system for a device for delivering fluids, comprising:
   a nozzle having one or more nozzle openings and an outer surface at a fluid outlet side of the nozzle;
   a nozzle holder which comprises a through-bore having a sidewall initiating at a position in communication with the one or more nozzle openings of the fluid outlet side of the nozzle, and terminating at an end face of the nozzle holder,
   wherein at least one of the following surfaces include at least one of elevation and/or depression microstructures and elevation and/or depression nanostructures:
      the outer surface of the fluid outlet side of the nozzle,
      an outer surface of the end face of the nozzle holder, or
      the side wall of the through-bore of the nozzle holder; and
   a check nut engaging the nozzle holder and having an end face and a bore including a side wall thereof, which communicates with the through-bore of the nozzle holder and widens out continuously therefrom, wherein at least one of an outer surface of the end face of the check nut and the side wall of the bore of the check nut include at least one of microstructures and nanostructures.

7. The nozzle system according to claim 5 wherein a side of the through-bore that is remote from the one or more nozzle openings includes at least one of microstructures and nanostructures.

8. The nozzle system according to claim 4 wherein the nozzle comprises an outlet side and an inlet side.

9. A delivery device for fluids comprising a nozzle according to claim 1.

10. A delivery device for fluids comprising a nozzle system according to claim 4.

11. A delivery device according to claim 10 comprising a lower and an upper housing part mounted to be rotatable relative to one another, the upper part of the housing containing a spring housing with a spring which is tensioned by rotating the two housing parts by means of a locking clamping mechanism and is released by pressing a release button on the upper part of the housing, the spring moving a power take-off flange connected to a piston on the lower end of which a container can be fitted, and at the upper end of which are found a valve and a pressure chamber which is connected for fluid transmission to the nozzle or the nozzle system formed in the upwardly open part of the upper housing part.

12. The delivery device according to claim 9 wherein the device is an inhaler or atomiser for delivering medicinal or pharmaceutical fluids.

13. A delivery device for pharmaceutical fluids according to claim 6, wherein the microstructures or nanostructures include surface structure elevations and/or depressions with a height/depth of 0.1 to 100 microns.

14. The delivery device for pharmaceutical liquids according to claim 13 wherein the spacing between the elevations and depressions are in the range from 0.1 to 200 microns.

15. The delivery device for pharmaceutical liquids according to claim 13 wherein at least 20% of the corresponding surface include the microstructures or nanostructures.

16. The delivery device for pharmaceutical liquids according to claim 13 wherein the elevations and/or depressions are formed by hydrophobic materials, glass and/or ceramics and/or metals and/or plastics selected from polyethylene, polypropylene, polycarbonate, polyacrylate, polyester and silanes.

17. The delivery device for pharmaceutical liquids according to claim 13 wherein the elevations and/or depressions are formed by subtractive or additive treatment of the surfaces, the treatment selected from stamping, etching, laser ablation, galvanic machining, adhesively attaching a structured film, adhesion of a powder, spraying with suspensions and depositing sublimates.

* * * * *